United States Patent
Donovan et al.

(10) Patent No.: US 7,627,534 B2
(45) Date of Patent: **\*Dec. 1, 2009**

(54) SYSTEM AND METHOD FOR STORING INFORMATION FOR A WIRELESS DEVICE

(75) Inventors: Mark C. Donovan, New York, NY (US); Paul M. Zeltzer, Encino, CA (US); Richard Kletter, Venice, CA (US); Jed Stafford, Seattle, WA (US); David M. Feinleib, Palo Alto, CA (US); Geoffrey Deitz, Studio City, CA (US); Scott Kramer, legal representative, Studio City, CA (US)

(73) Assignee: GoMed LLC, Brooklyn, NY (US)

( * ) Notice: Subject to any disclaimer, the term of this patent is extended or adjusted under 35 U.S.C. 154(b) by 215 days.

This patent is subject to a terminal disclaimer.

(21) Appl. No.: 11/450,321

(22) Filed: Jun. 12, 2006
(Under 37 CFR 1.47)

(65) Prior Publication Data
US 2007/0078784 A1    Apr. 5, 2007

Related U.S. Application Data

(63) Continuation of application No. 11/271,736, filed on Nov. 14, 2005, now abandoned, and a continuation-in-part of application No. 10/100,028, filed on Mar. 19, 2002, now Pat. No. 6,970,827.

(51) Int. Cl.
*G06F 17/60* (2006.01)
(52) U.S. Cl. .............................. 705/74; 705/72; 705/51
(58) Field of Classification Search .................. 705/74, 705/72, 51
See application file for complete search history.

(56) References Cited

U.S. PATENT DOCUMENTS

| 6,044,349 A * | 3/2000 | Tolopka et al. ................. 705/1 |
| 2003/0182232 A1 | 9/2003 | Zeltzer et al. |
| 2004/0167800 A1 | 8/2004 | Chang et al. |
| 2005/0021375 A1 | 1/2005 | Shimizu et al. |

FOREIGN PATENT DOCUMENTS

JP    2007279893 A  * 10/2007

* cited by examiner

*Primary Examiner*—Pierre E Elisca
(74) *Attorney, Agent, or Firm*—David R. Yohannan; Kelley Drye & Warren LLP (57) ABSTRACT

A system and method for storing personal, medical, and insurance related information on a wireless device are disclosed. The information may be stored by sending it from a remote personal computer to a central database using the Internet. The information may be stored on the central database. The information may be accessed on the wireless device (e.g. on a display) or sent from the wireless device or a central database to remote locations, such as a doctor's office or hospital.

18 Claims, 10 Drawing Sheets

Medical Information Summary
*Joan Q. Simple*
Address:
555 Hall Street
Beverly Hills, CA 90210-1311

DOB: 11/10/1948
Sex: FEMALE
SSN: 123-45-6789

Home Phone: 310-2713333
Work Phone: 323-333-5555

Insurance Information:
Primary Company: Any HMO
Policy Number: 9876543
Group Number: 489208
Phone Number: 877-568-2273
Precertification: 877-568-2273
Address: 123 Pismo Lane
City, State ZIP: Los Angeles, CA 90066
Phone Number: 310-555-2273
Secondary Company: N/A
Policy Number: 1234567
Group Number: 5967
Phone Number: 877-123-4567
Guarantor: Jack X. Simple
Employer: Self employed
SSN: 012-345-6789

Medications:
Imitrex 25 mg q 4h
Calcium/ Vit D 500mg bid
Fosamax 10 qD
Estrogen 0.625 qD
Lipitor 20 mg q hs
Insulin Lente 15 units q am Procedures:
Cholecystectomy 5/13/1986
Breast Biopsy 11/3/1993
Irradiation Chest wall (R) 3600cGy 2/1/1994
Tubal Ligation 8/13/1975
Hysterectomy 2/2/1994

Immunizations:
Hepatitis B 3/14/1993
Hepatitis B 8/14/1993
Hepatitis B 4/7/1994
Td 10/19/1997
Influenza 11/11/1993
Rubella 6/22/1971
TB Skin Test 9/11/1995 (Negative)

Emergency Contact:
Name: John X. Simple
Relationship: Husband
Phone: Home: 213-555-5678
Work: 213-555-2346

Medical and Hospital Information:
Hospital Preference: St Johns
Last Hospital Admission: Presbyterian
Admission Date: 5 June 1997
Blood Type: O+
Form Verified by Medical Professional: Yes
Organ Donor: No
Living Will: Yes Health Care Provider:
Dr. Jones (Gynecology) 213-555-0841
Dr. Schiff (Cardiology) 213-555-6449
Dr. Philips (Oncology) 213-555-9401

Diagnoses:
Migraine Headache without aura 1982
Hypertension 1980
Diabetes 1990
Breast Cancer (intraductal) 1993

Allergies:
Penicillin
Sulfa
Morphine
Keflex

> Verbally Confirm Additions and Changes with The Patient

SYSTEM AND METHOD FOR STORING INFORMATION FOR A WIRELESS DEVICE

CROSS REFERENCE TO RELATED APPLICATIONS

This application relates to, claims the priority of, and is a continuation of U.S. patent application Ser. No. 11/271,736 filed on Nov. 14, 2005, now abandoned and entitled "System and Method for Storing Information on a Wireless Device" which relates to, claims the priority of, and is a continuation-in-part of U.S. patent application Ser. No. 10/100,028 filed on Mar. 19, 2002, now U.S. Pat. No. 6,970,827 and entitled "System and Method for Storing Information on a Wireless Device." The entire contents of these applications are hereby incorporated by reference.

FIELD OF THE INVENTION

The present invention relates to a system and method for storing information on a wireless device. In particular, the present invention is directed to a system and method for storing on a wireless device, personal, medical, and insurance information that may be viewed on the wireless device and transmitted to other destinations by telefax, email, or other communications.

BACKGROUND OF THE INVENTION

Changes in mobility in the work force have led many consumers to change health care providers at least as frequently as they change jobs. The mobility of medical records, however, has not kept pace with the mobility of consumers. Most medical records are still recorded in written form at a doctor's office, either on paper or in a computer. Few consumers go to the trouble of maintaining their own private "database" of their medical history. As consumers switch from one provider to the next, they often lose access to crucial personal medical records and health-related insurance information. Even those consumers fortunate enough to have access to their records must go through the trouble of requesting and compiling the records in paper form. As a result, many consumers do not have and cannot provide their complete medical records, including personal medical histories, and records of immunizations, prescriptions and allergies. As a result of this situation, business travelers may find themselves in a new doctor's office without easy access to records. Parents may be unable to provide accurate information about their children. Emergency patients may jeopardize their health without ready access to accurate records. Even the typical medical consumer cannot provide or access their complete records during a routine doctor's office visit. Accordingly, a method and device for providing medical, insurance, and personal information in such instances would be helpful to such consumers.

Changes in the medical care delivery system and an aging population also contribute to the growing need for personal medical information that is readily accessible at any time (i.e., portable) and easily conveyed to medical service providers. More consumers are visiting multiple doctors and specialists than in the past. The need for multiple doctors affects the elderly, chronically ill, managed care patients, and parents with several children especially. Patients are required to fill out multiple forms with each new visit. Without portable, readily accessible information, consumers spend unnecessary time recalling enrollment data and filling out form after form. Ready access to one complete source of such information would greatly enhance the efficiency and accuracy of the medical system.

Furthermore, problems often arise with elderly patients who need to take multiple medications. It is common for such patients to face difficulties in recalling all of their medications and the correct dosages and dosage times. Thus, there is need for a method and device that provides simple, easy, and portable access to medical information, as well as daily medication reminders.

Furthermore, patients who visit multiple specialists may be prescribed medications by different physicians that interact adversely with one another. Easy access to information on a patient's prescriptions could also help to alleviate this problem.

Several systems for providing mobile access to personal medical information are known. One system stores consumer data on credit-card sized "smart cards." Smart cards are portable data carriers that are embedded with a computer chip that contains a user's personal medical information. The cards are read by smart card readers located in participating emergency response vehicles and by PC-based readers in participating hospitals, physicians' offices, pharmacies, and retirement facilities.

McGauley et al., U.S. Pat. No. 5,899,998, is directed to a system of storing personal medical information on smart cards, which may be accessed and updated at PC-based point-of-care stations. Data is entered at a PC station and transferred to a patient's smart card through off-line communications. Data stored on the card may be accessed at any point-of-care station. The patient's data is not sent to the portable device from a server through on-line communications. Instead, distributed databases may be used to update a patient's information through off-line coupling between a point-of-care database and a smart card database. The data is updated by detecting information that is stored on one database and not the other and automatically propagating the most recent data. This system requires both physical presence of the smart card at the point-of-care computer and a card reader for updating the information stored on the card. The physical presence requirement leads to inefficiencies because users cannot gain access to, or update, their information outside the presence of a reader station. Additionally, with smart cards there has been lack of standardization of the technology resulting in poor market penetration of card readers. The cell phone offers a universally accepted platform with high market penetration.

Accordingly, there is a need for a system and method that provides users with easy updating access through on-line communications. There is also a need for a system that provides increased portable accessibility to a user's information as it allows a user to view information at any time and place.

Another known system used to access personal medical information uses the Internet. Many websites offer to store online health care records for consumers. Consumers, however, are concerned with the privacy and security of the web as a place to store their vital, personal information. Hence, such sites have failed to gain broad consumer acceptance.

Thus, there is a need for a method and system that resolves the portability, privacy, and security problems of on-line storage of health care records. More particularly, there is a need for a system that provides users with easy access to their information without the security risk of storing it in a central location that can be hacked into.

Call center clearinghouses are another known form of access to personal health information, which have been used in emergency situations. Subscribers to these services wear identification bracelets with toll free numbers engraved on them. Although these services have gained limited acceptance, consumers may not want to wear the jewelry, because it is viewed as a sign of illness or weakness; in addition, valuable time may be lost in emergency situations by calling the toll free number and waiting to retrieve the patient's medical data. The call center system also does not scale well to handle a large number of calls because of prohibitive labor cost. Thus there is a need for an efficient method to access personal medical information without the need to call and wait for an intermediary to retrieve the data.

Although not related to the medical information field, Martino, U.S. Pat. No. 5,805,676 discloses a system in which data is entered into a data transaction device, which is also a telephone, for transmission and storage on a database server. This data, however, is not locally stored on the telephone device and thus presents security risks.

Accordingly, there is a need for a method and system that provides for storage of the user's information.

OBJECTS OF THE INVENTION

It is therefore an object of a preferred embodiment of the present invention to provide a system and method for a user to carry medical, insurance, and personal information on their person at virtually all times.

It is another object of an embodiment of the present invention to provide a system and method for storing personal, medical, and insurance information on a wireless device.

A further object of an embodiment of the present invention is to provide portable and efficient access to personal, medical, and insurance information.

An additional object of an embodiment of the present invention is to provide secure access to personal, medical, and insurance information.

Another object of an embodiment of the present invention is to provide a system and method for securely transmitting essential health information from a wireless device to health care providers.

It is yet another object of an embodiment of the present invention to provide a system and method for storing personal, medical, and insurance information that can be updated easily.

It is still another object of an embodiment of the present invention to provide a system and method for storing personal, medical, and insurance information that can be password-protected for selective access.

Yet another object of an embodiment of the present invention is to provide a system and method for storing information on a wireless device that deletes the information if the device is lost or stolen.

Yet another object of an embodiment of the present invention is to provide a system and method for storing medical information that gives medication reminders to users.

It is still yet another object of an embodiment of the present invention to provide a system and method for storing information locally on a wireless device instead of on an Internet accessible database or an on-line database, thereby improving user confidence in its security.

It is therefore an object of an embodiment of the present invention to provide a system and method for a user to have universal access to their personal health records stored on a central server by way of a wireless device.

It is another object of an embodiment of the present invention to provide a system and method for unlocking personal, medical, and insurance information on a central server using the unique hardware ID of a wireless device as a key.

A further object of an embodiment of the present invention is to provide portable and efficient access to personal, medical, and insurance information.

An additional object of an embodiment of the present invention is to provide secure access to personal, medical, and insurance information.

Another object of an embodiment of the present invention is to provide a system and method for securely transmitting essential health information from a central server to health care providers by means of using a wireless device's unique hardware ID to unlock this information.

It is yet another object of an embodiment of the present invention to provide a system and method for storing personal, medical, and insurance information that can be updated easily.

It is still another object of an embodiment of the present invention to provide a system and method for storing personal, medical, and insurance information that can be password-protected for selective access.

Yet another object of an embodiment of the present invention to provide a system and method for storing personal, medical, and insurance information that can be protected for selective access by a unique hardware ID of associated to a wireless device.

Additional objects and advantages of the invention are set forth, in part, in the description which follows and, in part, will be apparent to one of ordinary skill in the art from the description and/or from the practice of the invention.

Additional objects and advantages of the invention are set forth, in part, in the description which follows and, in part, will be apparent to one of ordinary skill in the art from the description and/or from the practice of the invention.

SUMMARY OF THE INVENTION

Responsive to the foregoing challenges, Applicants have developed an innovative method for storing information on a wireless device, comprising the steps of:

accessing a central server, said central server having at least one database associated therewith; storing personal, medical or insurance information relating to a person on the central server database; accessing the central server with the wireless device; and transferring at least a portion of the information from the central server to a terminal.

accessing a central server, said central server having at least one database associated therewith; temporarily storing personal, medical or insurance information relating to a person on the central server database; accessing the central server with the wireless device; transferring the information from the central server to the wireless device; storing the information in the wireless device; and deleting the information from the central server database.

Applicants have also developed an innovative method for storing information on a wireless device, comprising the steps of: accessing a central server with a remote input device, said central server having a database associated therewith; temporarily storing information relating to a person in the central server database; storing in the database a password or PIN associated with the information; accessing the central server with a wireless device; transmitting the password or PIN from the wireless device to the central server; transmitting the information temporarily stored in the database to the wireless device responsive to the receipt of the password or PIN by the central server; storing the information in the wireless device; and deleting the information temporarily stored in the central server database.

Applicants have developed an innovative system for storing information on a wireless device comprising: a central server; a database operatively connected to the central server; a remote input device; a network connecting the remote input device to the central server; a wireless device having a memory; medical information relating to a person stored in the wireless device memory in the form of a URL; dedicated means for accessing the medical information from the memory; and a wireless network connecting the wireless device to the central server.

Applicant have developed an innovative method for storing and retrieving information using a wireless device, comprising the steps of: accessing a central server, said central server having at least one database associated therewith; storing personal, medical or insurance information relating to a person on the central server database; accessing the central server with the wireless device; securing the information in the central server database responsive to receipt of a key from the wireless device; and transferring at least a portion of the information from the central server to a terminal responsive to receipt at the central server of the key from the wireless device at a later time.

Applicant have developed an innovative method for storing and retrieving information using a wireless device, comprising the steps of: accessing a central server, said central server having at least one database associated therewith; storing personal, medical or insurance information relating to a person on the central server database; accessing the central server with the wireless device; securing the information in the central server database responsive to receipt of a key from the wireless device; and transferring at least a portion of the information from the central server to the wireless device responsive to receipt at the central server of the key from the wireless device at a later time.

It is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention and, together with the detailed description, serve to explain the principles of the present invention.

BRIEF DESCRIPTION OF THE DRAWINGS

In order to assist the understanding of this invention, reference will now be made to the appended drawings, in which like reference numerals refer to like elements. The drawings are exemplary only, and should not be construed as limiting the invention.

FIG. 4 is a printout of a hypothetical user's personal, medical, and insurance information according to an embodiment of the present invention.

DETAILED DESCRIPTION OF PREFERRED EMBODIMENTS OF THE INVENTION

Figure 1:
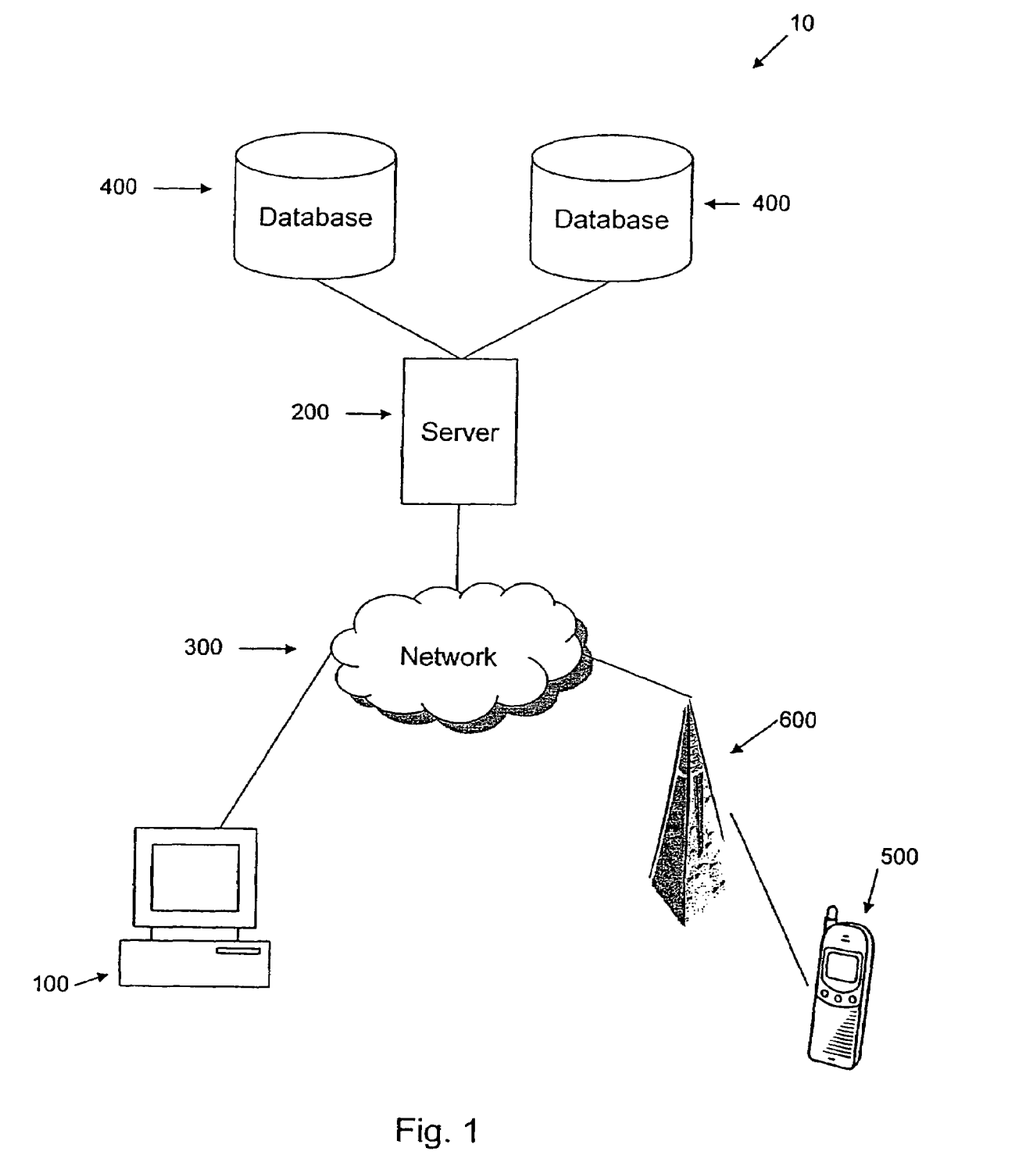
FIG. 1 is schematic diagram illustrating a system for storing information on a wireless device according to a first embodiment of the present invention.

Reference will now be made in detail to system and method embodiments of the present invention for storing information on a wireless device, an example of which is illustrated in the accompanying drawings. With reference to FIG. 1, in a first embodiment of the present invention a system 10 for storing information on a wireless device is shown. The system 10 may comprise: a central server 200 having one or more databases 400 associated therewith; means 100 for providing information to the central server; a network 300; a wireless device 500; and means 600 for transferring the information from the server 200 to the wireless device 500.

With continued reference to FIG. 1, the means for providing information to the central server 200 may comprise one or more remote input devices 100, such as a personal computer. Although a personal computer is shown in FIG. 1, it is appreciated that the remote input device 100 could be provided by a Personal Digital Assistant (PDA), two-way pager, wireless telephone, PDA phone, conventional telephone, wireless web phone, handheld PC, tablet, laptop, or other suitable communication device without departing from the scope of the present invention.

The remote input device 100 may be connected to a server 200 over a network 300. The network 300 may be any suitable communications network that is compatible with both the input device 100 and the server 200. The network 300 may include hard-wired components, wireless components, or some combination of the two. In the preferred embodiment, the network 300 may comprise and/or include the Internet.

The server 200 may be connected to the network 300 such that communications may be made from numerous remote input devices 100 to a single server. The server 200 facilitates the receipt and temporary storage of information, as well as the transmission of stored information, as is described in more detail below. The server 200 is provided with the protocols necessary for communication with the remote input devices 100 and with the wireless devices 500.

One or more databases 400 may be associated with the server 200. The databases 400 may be adapted to store personal, medical, and insurance information relating to a user. The databases 400 may also be used to store a user name, password, and/or Personal Identification Number (PIN) relating to a user. The databases 400 are preferably capable of storing and providing content used for web-based and Wireless Application Protocol (WAP)-based applications of the system. In the preferred embodiment, databases 400 are located on one or more web servers 200. Other configurations and locations of the databases would be well known to persons of ordinary skill in the art and are considered within the scope of the present invention.

Content stored on databases 400 may include applications for obtaining information from users, including a web-based information form, such as a medical information form. The databases 400 may also include temporary storage for the information received from users, as well as applications for transmitting the information to a wireless device. The databases 400 may further include applications that enable the transmission of information back from a wireless device to a remote recipient via text-message, email, facsimile, voice, etc. Also, the servers may include applications which allow for natural language information being sent to the wireless device, to be translated into codes, thereby taking up less space on the wireless device.

In one possible implementation, compression or lookups (e.g. D=Diabetes) may be used to allow for encoding maximum user data. Form based information can be encrypted for added security and to reduce the amount of required storage space on the wireless device, by using abbreviated codes for diseases (adhering to standards set forth by HIPAA, the Health Insurance Portability and Accountability Act and existing medical diagnosis (ICD-9) or drug (NDC) codes. For example, an NDC code for 30 mg of Prozac would be stored as 00002400630). Conversely, when data is retrieved from the wireless device and sent out to a fax machine, these database servers would translate the codes back into natural language and format them appropriately.

Figure 5:
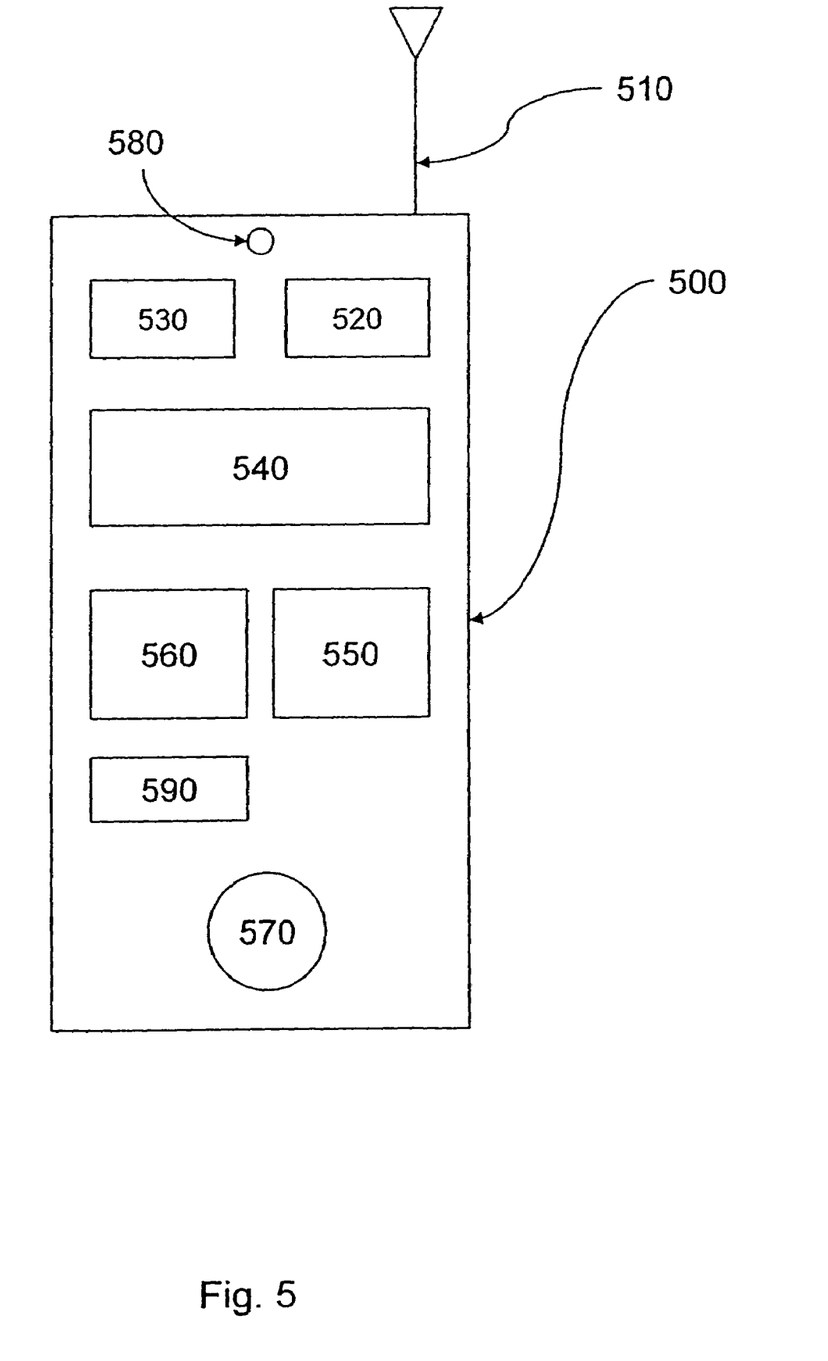
FIG. 5 is a schematic diagram of a wireless device that may be used in an embodiment of the invention.

One or more wireless devices 500, such as a cellular phone or a PDA, may be connected to the server 200 over the network 300. An example of a wireless device 500 is shown in FIG. 5. The wireless device may include one or more of the following in some functional form: an antenna 510, a transceiver 520, a memory 530, a display screen 540, a keypad 550, a wireless browser 560, a microphone 570, a speaker 580, and a clock/calendar 590. The wireless device 500 may communicate with the network 300 via a wireless service provider. The wireless device 500 is preferably provided with a wireless browser functionality and associated memory. The wireless browser enables communication with the server 200, and the associated memory enables storage of information downloaded from the server.

Wireless service providers may establish connections between wireless devices and the network 300 (preferably the Internet) by a dial-up server and communications towers 600. The connection between the wireless device 500 and the server 200 preferably enables user-input information that has been stored on the databases 400 to be sent from the server 200 to the wireless device 500 for storage thereon. The transmissions between the server and the wireless device may be protected by security measures, such as Wireless Transport Layer Security (WTLS), Secure Sockets Layer (SSL), or other means of encrypting transmitted data.

Figure 2:
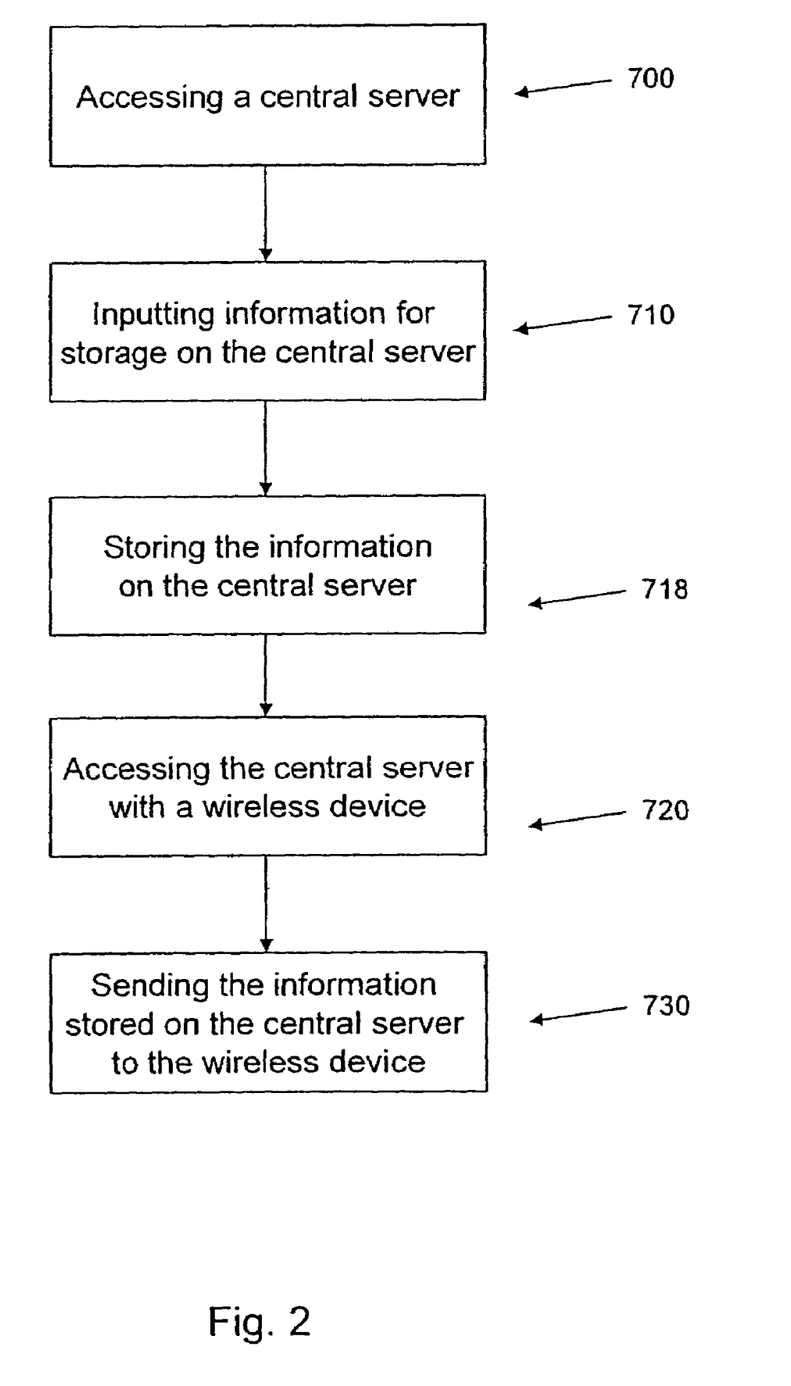
FIG. 2 is a flowchart of a method embodiment of the present invention for storing information on a wireless device.
Figure 6:
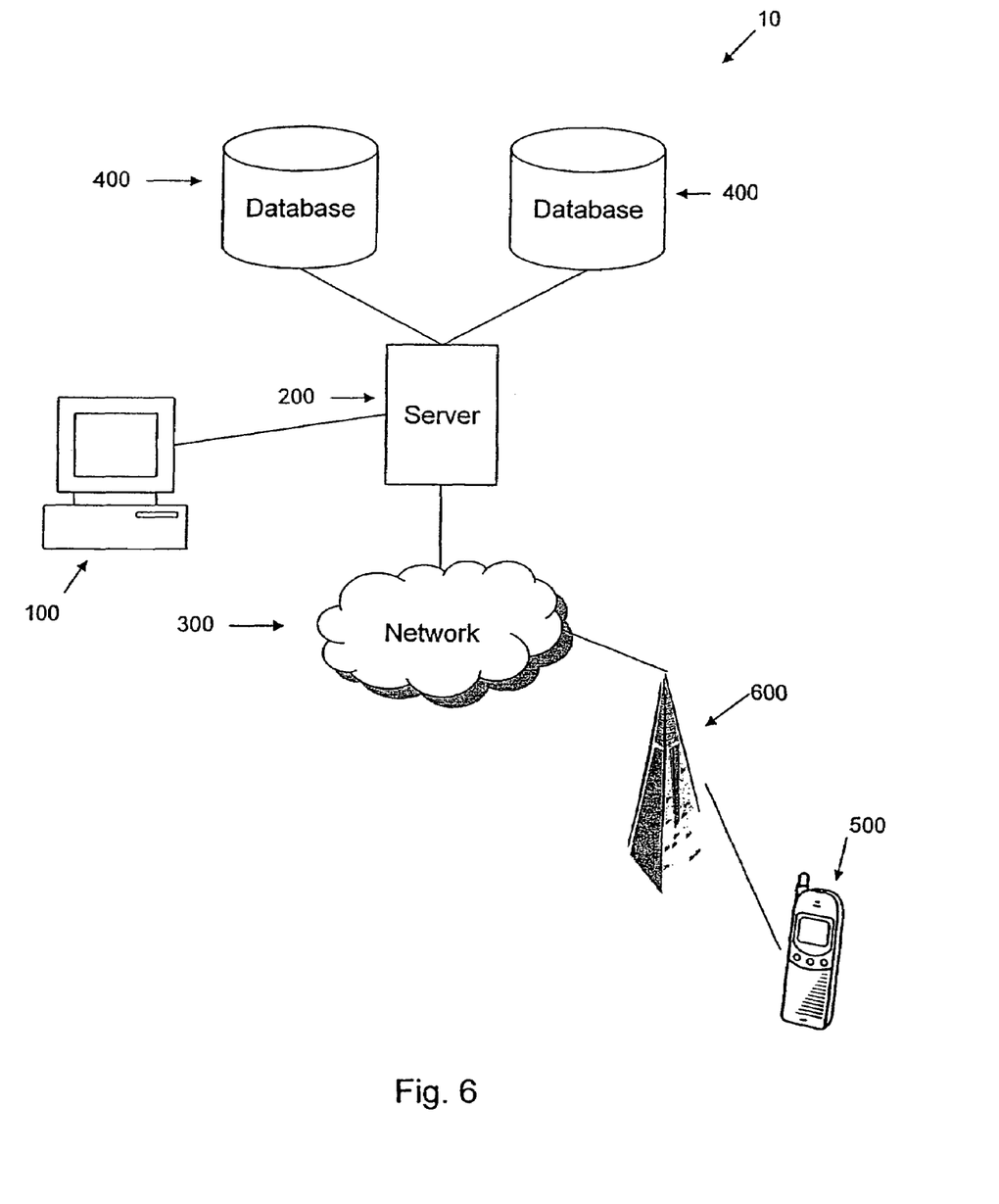
FIG. 6 is a schematic diagram illustrating an alternative embodiment of the invention.

A method for storing information on the wireless device 500 in accordance with an embodiment of the invention is shown in FIG. 2. With reference to FIGS. 1 and 2, a central server 200 may be accessed in step 700. Preferably the central server 200 is accessed by a remote input device 100 as described above. It is possible, however, to access the central server from a terminal that is local to or co-located with the central server (as shown in FIG. 6). Access may involve logging onto the server 200, requesting information and forms used to input information, and downloading the information and forms from the central server and the databases 400 associated with the central server. When an embodiment of the invention is implemented in a web-based environment, the web-based information forms may be displayed for users on the screen of the input device, such as the personal computer 100 shown in FIG. 1.

In step 710, a wide variety of medical, personal, and/or insurance information may be input on a remote (or even local) input device. The input information (shown in FIG. 4) may include, but is not limited to: name; address; home and work phone; date of birth; sex; social security number; emergency contacts; medical and hospital information, such as hospital preference, last hospital admission, blood type, organ donor, and living will designations; allergies; diagnoses; surgical procedures; medications; health care providers; user's doctor's name and contact information; immunizations; health insurance information; and dates issued and last updated. This list is not considered to be exhaustive, but rather exemplary. It is appreciated that any information that generally falls under the category of medical, insurance, and personal information may be input by the user or someone else on his behalf.

The input information may be inserted into an on-screen form. After the information is input at the remote device 100, in step 718 it may be sent via the network 300 to the server 200, which in turn may store the information in the databases 400. The information may be sent to the server 200 using normal Internet protocols, such as HTML. The user may associate a user name and/or password with the information stored on the databases 400. The user name and/or password may be used by the user to access the information from the databases at a future time and instruct the transfer of the information to a wireless device.

The server 200 may be instructed to store the information in the databases only temporarily, e.g. for no more than twenty-four (24) hours. After the specified temporary storage time, the information may be deleted from the databases 400. Alternatively, the information may be stored in the databases 400 until it is accessed by and downloaded to a user's wireless device 500. The temporary storage of the information in the databases acts as a security measure for the information. Once the temporary storage period comes to an end, there is no central location from which a user's medical information can be accessed.

With continued reference to FIGS. 1 and 2, in step 720 the central server may be accessed by a wireless device 500 during the time that the information is temporarily stored in the databases 400. Using a wireless protocol, such as WAP, the wireless device 500 may request that the information that is temporarily stored in the databases be downloaded into memory provided in the wireless device. The user may need to provide a user name and/or password before being granted access to, and a download of, the information.

Provided that the user of the wireless device 500 is authorized (as evidenced by use of the correct user name and password, for example), the information stored in the databases may be transmitted to the wireless device in step 730. The information sent to the wireless device 500 may be stored in memory resident in the wireless device. Data may be stored in a HIPAA approved coded form.

Figure 3:
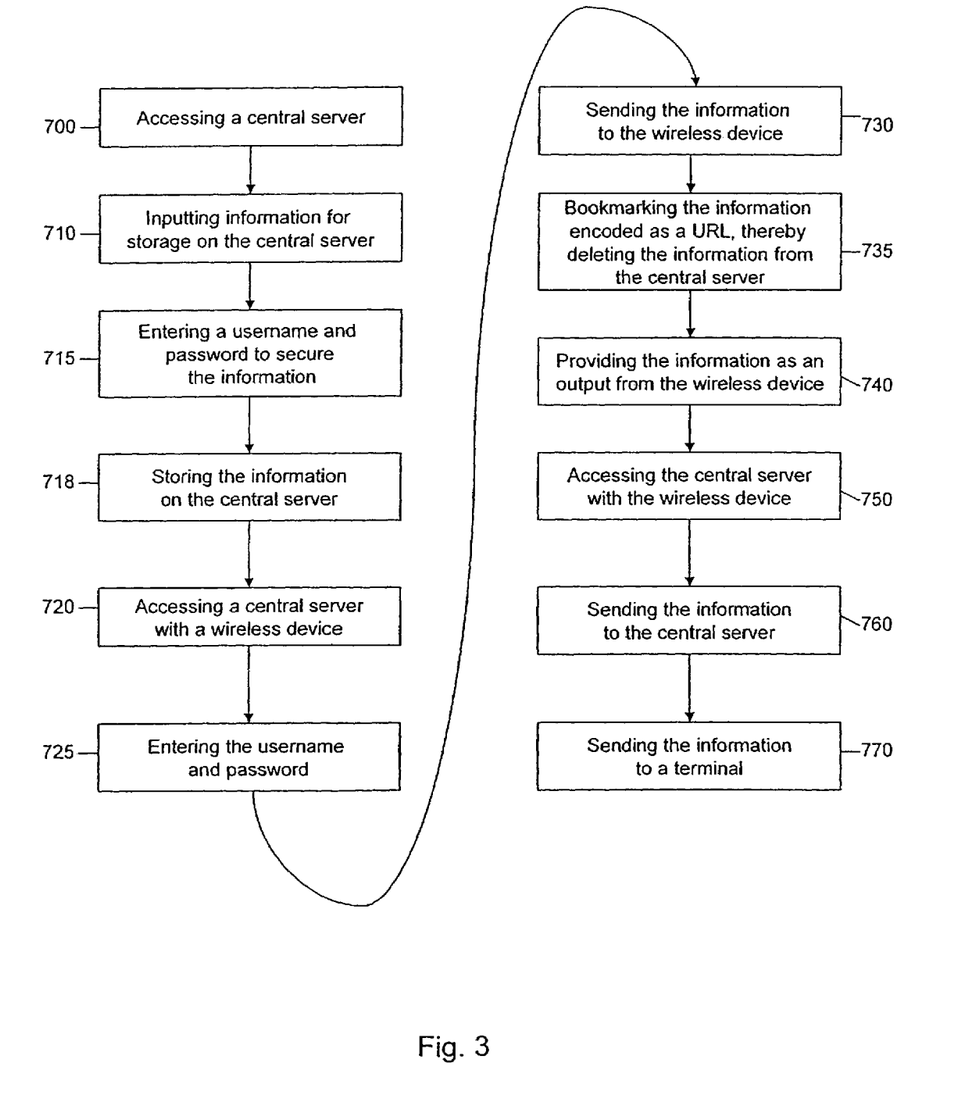
FIG. 3 is a flowchart of a method embodiment of the present invention for storing information on a wireless device and transmitting the information from the wireless device to a remote location.

The steps of a preferred method embodiment of the present invention are shown in FIG. 3. With reference to FIGS. 1 and 3, in step 700 a user accesses a central server 200 over the network 300 via an Internet web site using the remote terminal 100. Preferably, the databases 400 retrieve the web-based content for the Internet web page and display the content on the computer 100, or other suitable device. The computer screen preferably displays an information form for a user to fill out.

In step 710 the user may input information into the form at the remote terminal 100 for storage on the central server 200, which may be health care information, including personal identification, medical, pharmacy, and insurance information. Examples of the types of information that may be input are provided above. In step 715, the user may also designate a user name and password or PIN at the time that the information is input in order to protect against disclosure of the information to unauthorized individuals. The user name and/or password may be set by the user or assigned by the system.

The user may choose to password protect all or only part of the information. The stored information may be segregated by the user into tiers, with each tier having a predetermined level of security. A simple system may be implemented with two tiers of security. For example, in a two tiered system the user may choose to designate personal information such as Name, Address, Emergency Contact Information, etc. to be viewable on the wireless device display (provided the device supports such a configuration). The foregoing basic information would be visible to any operator of the wireless device, but private information, such as prescriptions, past medical history, etc. would be encrypted and/or protected by password. The information that is intended to be protected may be tagged at the time that it is input by the user or his agent. Multiple tiers of security may be provided by using different and more complex encryption and password protection for the different tiers.

Additional security measures may also be used to protect the connection between the computer 100 and the central server 200 while a user inputs data for storage. Digital links and encryption (e.g. SSL) may be used to protect data transmitted between the computer and the server. It is expected that only SSL will be used to protect the link between the computer 100 and the central server 200, as this is the standard protection employed by financial institutions for the secure transfer of information.

In step 718 the information may be sent from the remote device 100 to the server 200, which in turn may store the information in the databases 400. The information may be only temporarily stored on the central server to preserve its confidentiality. The databases 400 serve as a temporary storage that enables communication between the user's computer 100 with his wireless device 500.

Figure 7:
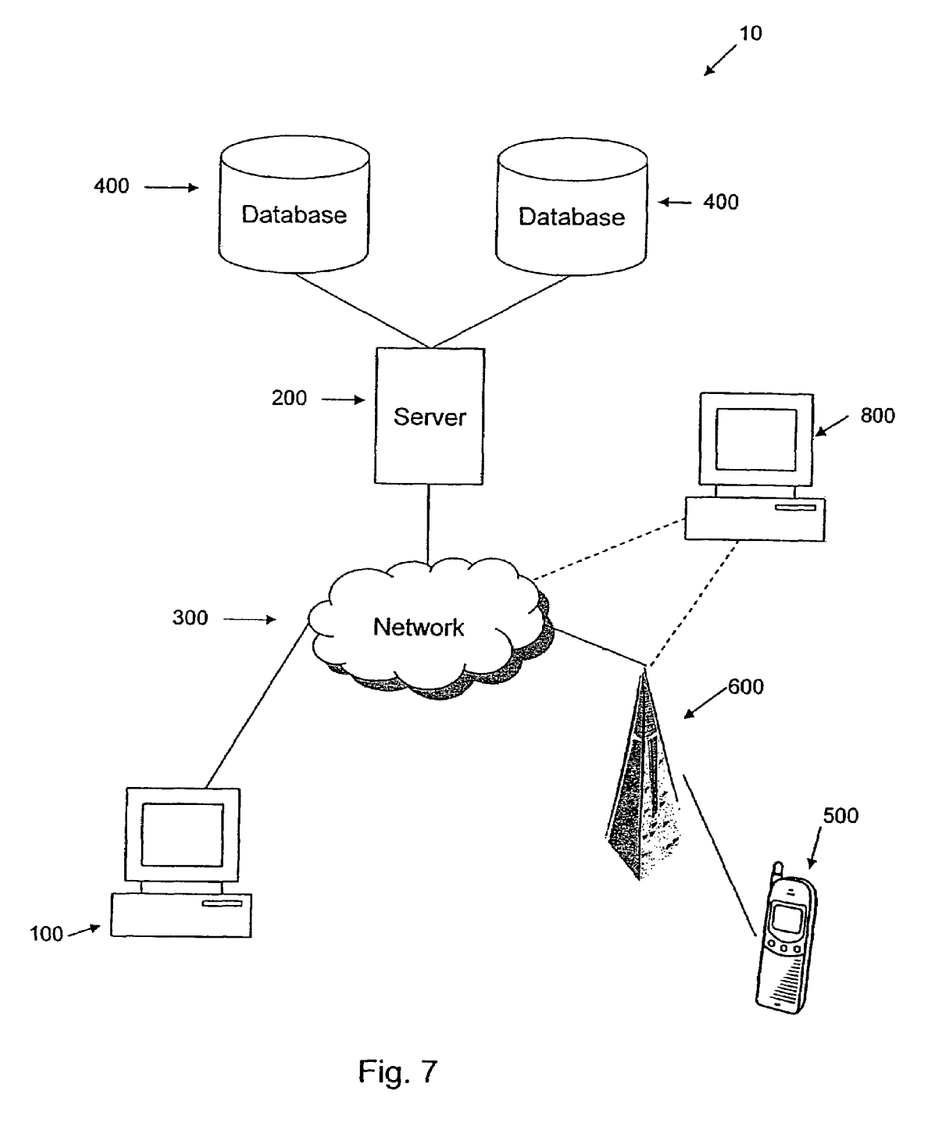
FIG. 7 is a schematic diagram illustrating an alternative embodiment of the invention.

With reference to FIG. 7, if a direct connection between the computer 100 and the wireless device 500 is available, in an alternative embodiment, the information could be sent directly between the two without the need for storage in the databases 400. This may be accomplished using any type of connection to the wireless device whether it be USB, IrDA, Cellular Network, or others. It could also be realized using technology such as Java, BREW, or future languages.

Looking to the future, the proliferation of the use of languages such as Java/J2ME and BREW in conjunction with wireless communications will enable users to launch a Java (or similar) based application directly from the wireless device. Downloaded information from the central server 200 can be stored without having to "bookmark" it. The information may instead be stored locally and provided by direct transmission from the wireless device to locations such as health care provider computers and fax machines. Enhancements may also enable the storage of compressed graphics on the wireless device, thereby allowing a user's MRI or CT scans to be stored on the device.

After the information is stored on the central server 200 of the system, the central server may be accessed by the wireless device 500 in step 720. The wireless device 500 may connect to a wireless carrier's dial-up server using a wireless browser and establish a lower level connection with the network 300 and the central server 200 via a wireless communications system 600. After the browser function of the wireless device 500 is activated, the user may enter a Uniform Resource Locator (URL) to access an Internet web site maintained by the server 200. The request for the entered URL preferably is sent to a Wireless Application Protocol (WAP) gateway, which is located in the cellular provider's infrastructure. The WAP gateway provides communication between a WAP device (a wireless device) and the traditional Internet.

With renewed reference to FIGS. 1 and 3, the WAP gateway may request the URL with a Hypertext Transfer Protocol (HTTP) request. The central server 200 may receive the request and detect that the request is coming from the wireless device 500 (WAP device), so it retrieves a Wireless Markup Language (WML) version of the site from the databases 400. WML is a language used to implement web pages for devices that support WAP, such as, for example browser-enabled mobile phones. WML is a tag-based language used to describe pages of information to be displayed in a browser. WAP devices use WML, in part, because it requires less bandwidth compared to Hypertext Markup Language (HTML). WML is also faster and easier to render (e.g., translate and display) than HTML.

The content of the returned page, which is in WML, is sent to the WAP gateway. The textual WML may be compiled into tokenized WML at the WAP gateway. The tokenized WML content may then be sent to the wireless device 500. The browser on the wireless device 500 may display the tokenized WML code contents, such as by a page or screen, to a user. The contents may prompt a user to enter a username and password in accordance with step 725. A user preferably enters a username and password to obtain access to the information stored by the user in the databases 400. An entered username and password may be passed as a request to the central server 200, encoded as part of a URL.

After accessing the central server 200 with the wireless device 500 and entering a username and password, the server may send the information stored on the databases 400 to the wireless device in step 730. The server 200 may return a WML page containing the information, an example of which is shown in FIG. 4, using a URL. The returned URL may contain all of a user's information encoded within it, which may be personal, medical history, and/or insurance information. Because some wireless devices limit the length of a URL to a specific number of characters, compression or lookups may be used in a URL containing a user's information, such as for example D=diabetes. Lookups allow for encoding maximum user information.

An exemplary URL is: http://www.gomed.com/senddate.wml?f=joan?q=simple?l=doe?a=4510.bav.road?tet=1195?d=a.

The above URL is a basic example of the format the URL may take when storing user information, the information may also employ lookup tables and an encryption method to further protect user data in case the user lends the wireless device out and that borrower looks through the user's bookmarks on the device display.

After the information is received by the wireless device 500, the information may be saved on the wireless device and deleted from the central server 200, in step 735. A user may bookmark the URL returned by the central server 200, which marks and saves the site. The wireless device may have a dedicated key that allows a user to bookmark a URL. Alternatively, the wireless device may have a bookmark option in its browser menu.

Preferably, the bookmarked site appears on a browser menu of the wireless device. By bookmarking the URL, the information contained in the URL may be saved on the wireless device and deleted from the central server. Two events may trigger the user information to be deleted from the server.

In one embodiment, the information may be automatically deleted after the passage of a defined time period starting from the time that the information is entered on the server (e.g. 24 hours). In another embodiment, the information may be deleted after the user bookmarks the URL and verifies his information on the WAP device. After verification that the information is stored correctly, the user may be invited to select "verify" to confirm the information is correctly stored. The server may then delete the information from the interim database. Additionally, the application may include a safeguard that provides that, should a wireless device ever become lost, the information on the device may be deleted/removed from the device for final security purposes.

Once the information is deleted from the server, the user's information is only stored locally on the wireless device 500. A user's username, password, phone type, cellular provider, and/or usage information, may remain on the server databases 400, however, so that users may update the information. Before a user is permitted to update information using the server 200, the correct username and/or password may need to be provided. For privacy and security reasons, this is preferable to many consumers who do not wish to have their personal and medical information residing on the Internet.

After bookmarking and saving the information on the wireless device 500, the user may access the information as an output from the wireless device in step 740. The information may be visual or audible. Viewable information may be accessed by activating a designated button or selecting it from a browser menu on the wireless device. The designated button may have an emergency symbol on it to alert medical personnel that the device contains accessible medical information. Alternatively, the information may be provided audibly if the wireless device is provided with voice synthesis or voice storage capability. An audible rendition of the information may be especially useful for delivery of emergency information. Other suitable means of displaying or delivering a user's information on a wireless device may include text-to-voice capability.

The user may secure some or all of the information stored on the wireless device such that it can only be accessed after a password or PIN are input into the wireless device. On a PDA type device this may be implemented using custom software that controls access to the information stored on the device by prompting the user for the PIN or password before letting the user view the private information. On a cellular device this may be accomplished if the device supports custom Java applications and other technical advancements, which could prompt the user for the PIN to view the private information. In other instances, the private information may be stored in an encrypted URL format on the wireless device. If the user chooses to launch the wireless GoMed URL, he may view all of the private information on the device without sending it to anyone else.

With reference to FIG. 7, the user may transmit the information to another destination 800 through the server 200 or through some other communications route. The destination 800 may be a doctor's office, an insurance company, a hospital, or other location. The user may select the bookmark that is encoded with the information desired to be transmitted from the browser menu of the wireless device. With renewed reference to FIG. 3, in step 750, the central server 200 may be accessed by the wireless device 500 using the wireless browser function. In step 760, the complete bookmarked URL containing the user's personal, medical, and/or insurance information may be sent from the wireless device 500 to the central server 200. Alternatively, a portion of the URL, for example the non-password protected information, could be sent to the central server. The server 200 may return WML content that is displayed as a page, asking the user for destination information. The user may enter destination information to send the medical/insurance information to another terminal. In step 770, the central server 200 may be adapted to format the information and transmit it to the remote terminal 800 (FIG. 7) via e-mail, fax, or any other appropriate means of communication.

In a preferred embodiment, the wireless device 500 storing a user's medical information may also be adapted to provide reminders of when to take particular medicines. This functionality may be accomplished in a number of ways. In one embodiment, the wireless device may support applications such as custom Java applications in the background, which can alert the user with a reminder. In another embodiment, the user may enter personal information on the central server that indicates the times that medication is required. Alerts may then be sent down from the central server to the wireless device for receipt by the user. In yet another embodiment, the wireless device may receive a voice message reminder from the central server or in response to a signal generated by the clock/calendar functionality of the wireless device. Some wireless devices provide alerts, which may be accepted in to the device's reminder system (calendar) and used to later alert the user of the specified times for a particular event (such as medication). The foregoing functionality may be helpful to consumers, especially those taking multiple medications and the elderly.

In an alternative embodiment of the present invention, the user may input information for storage on the central server 200 and send the information to a wireless device 500, as described above. In the alternative embodiment, the wireless device 500 stores the information locally without the need for bookmarking a URL containing the information. The locally stored information may be viewed on a screen of the wireless device 500 or sent to a terminal 800 (FIG. 7) directly from the wireless device, rather than through a central server.

Figure 8:
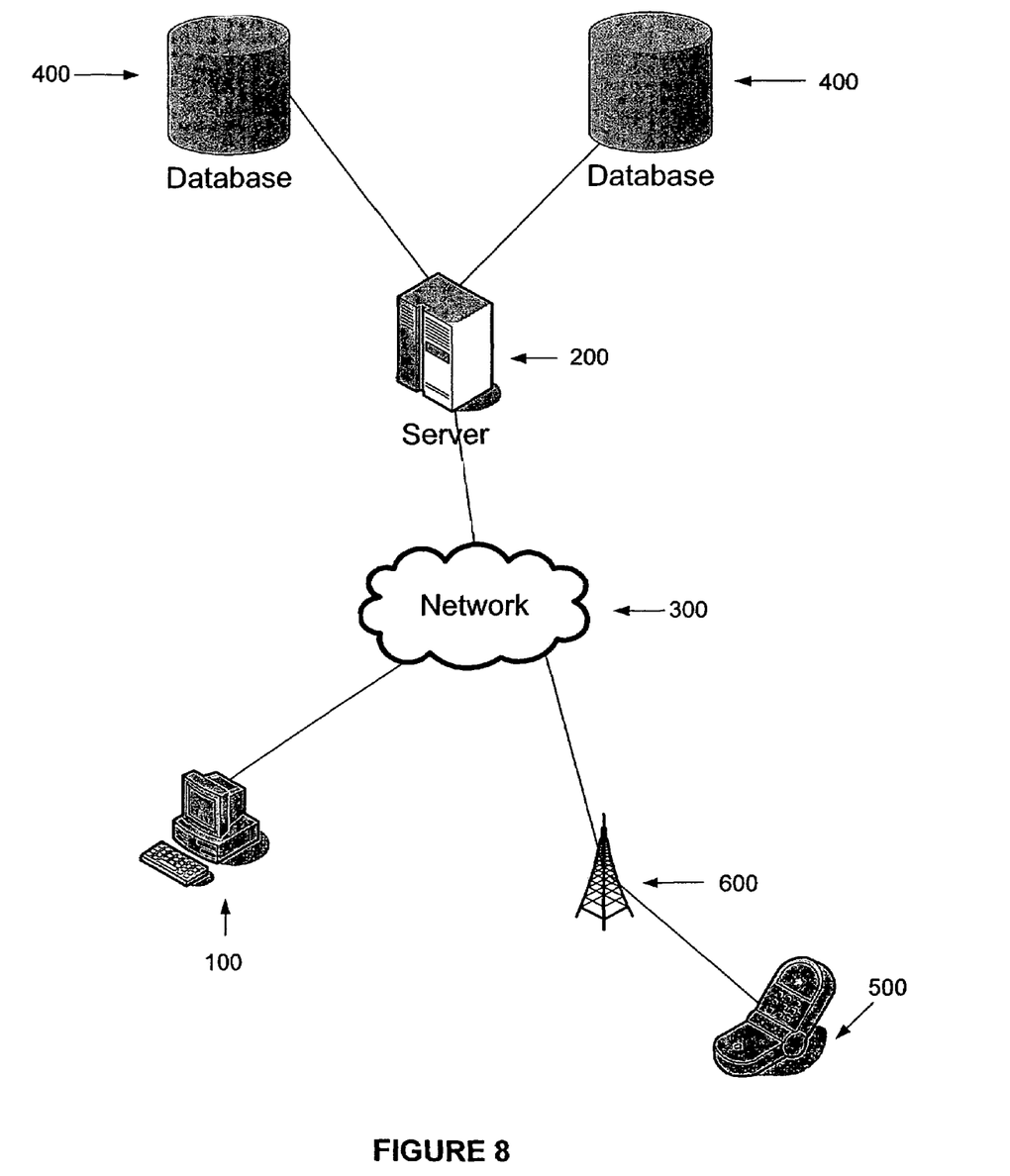
FIG. 8 is a schematic diagram illustrating an alternative embodiment of the invention.

FIG. 8 illustrates a system for storing sensitive information in a location from which it may be retrieved using a wireless device, such as a cellular telephone. The system shown in FIG. 8 may comprise one or more databases 400 which may be accessed by a central server 200 over a telecommunications link of any type (e.g., wired, wireless, etc.) The server 200 may be connected through one or more networks 300 to a terminal 100 adapted for manual or automated input of information such as medical, insurance, or other sensitive information. The one or more networks 300 may also provide communications between the central server 200 and a wireless device 500 through a wireless network 600, such as a cellular telephone network.

Figure 9:
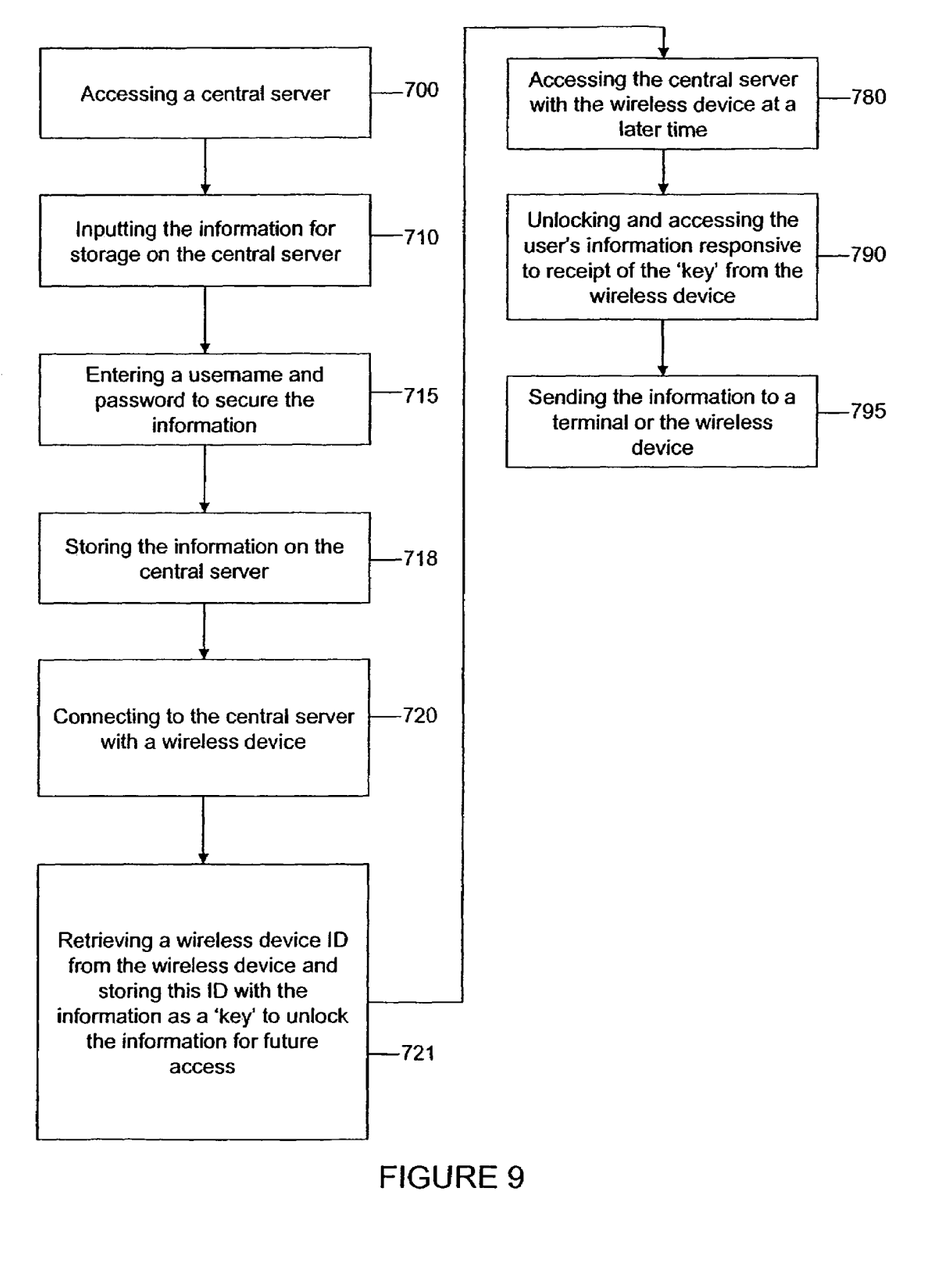
FIG. 9 is a flowchart of a method embodiment of the present invention for storing information on a central server, locking the information on the server with a unique hardware ID key of a wireless device, unlocking the information with this key and transmitting the information from the server to a remote location.

The steps of an alternative method embodiment of the present invention are shown in FIG. 9. With references to FIGS. 8 and 9, an embodiment of a method through which a user may store sensitive information such as personal medical, and/or insurance information for retrieval using a wireless device is shown.

In step 700 a user may access a central server 200 over the network 300 via an Internet web site using the remote terminal 100. The databases 400 may retrieve web-based content for an Internet web page and display content at a remote terminal 100, or other suitable device. The remote terminal 100 preferably may display an information form for the user to fill out.

In step 710 the user may input information at the remote terminal 100 for storage on the central server 200, which may be health care information, including personal identification, medical, pharmacy, and insurance information. Examples of the types of information that may be input are provided above. In step 715, the user may also designate a user name and password or PIN at the time that the information is input in order to protect against disclosure of the information to unauthorized individuals. The user name and/or password may be set by the user or assigned by the system.

The user may choose to password protect all or only part of the information. The stored information may be segregated by the user into tiers, with each tier having a predetermined level of security. A simple system may be implemented with two tiers of security. For example, in a two tiered system the user may choose to designate personal information such as Name, Address, Emergency Contact Information, etc. to be viewable on the wireless device display (provided the device supports such a configuration). The foregoing basic information would be visible to any operator of the wireless device, but private information, such as prescriptions, past medical history, etc. would be encrypted and/or protected by password. The information that is intended to be Protected may be designated at the time that it is input by the user or his agent. Multiple tiers of security may be provided by using different and more complex encryption and password protection for the different tiers.

Additional security measures may also be used to protect the connection between the computer 100 and the central server 200 while a user inputs data for storage. Digital links and encryption (e.g. SSL) may be used to protect data transmitted between the computer and the server. For example, SSL may be used to protect the link between the computer 100 and the central server 200, as this is the standard protection employed by financial institutions for the secure transfer of information.

In step 718 the information may be sent from the remote device 100 to the server 200, which in turn may store the information in the one or more databases 400.

After the information is stored on the central server 200 of the system, the central server may be accessed by the wireless device 500 in step 720. The wireless device 500 may connect to a wireless carrier's dial-up server using a wireless browser and establish a lower level connection with the network 300 and the central server 200 via a wireless communications system 600. After the browser function of the wireless device 500 is activated, the user may enter a Uniform Resource Locator (URL) to access an Internet web site maintained by the server 200. The request for the entered URL preferably is sent to a Wireless Application Protocol (WAP) gateway, which is located in the cellular provider's infrastructure. The WAP gateway provides communication between a WAP device (a wireless device) and the traditional Internet.

The WAP gateway may request the URL with a Hypertext Transfer Protocol (HTTP) request. The central server 200 may receive the request and detect that the request is coming from the wireless device 500 (WAP device), so it retrieves a Wireless Markup Language (WML) version of the site from the databases 400. WML is a language used to implement web pages for devices that support WAP, such as, for example browser-enabled mobile phones. WML is a tag-based language used to describe pages of information to be displayed in a browser. WAP devices use WML, in part, because it requires less bandwidth compared to Hypertext Markup Language (HTML). WML is also faster and easier to render (e.g., translate and display) than HTML.

The content of the returned page, which is in WML, is sent to the WAP gateway. The textual WML may be compiled into preferably tokenized WML at the WAP gateway. The tokenized WML content may then be sent to the wireless device 500. The browser on the wireless device 500 may display the tokenized WML code contents, such as by a page or screen, to a user.

In step 721, the central server may prompt a user to enter a username and password on the wireless device 500 and retrieve a wireless device ID from the wireless device 500. In one embodiment, the wireless ID may be a cell phone number. In a further preferred embodiment, the wireless device ID may be a unique hardware ID. A unique hardware ID may uniquely identify a particular wireless device, and unlike a cell phone number, may be difficult to copy.

A user preferably enters a username and password to associate the wireless device ID with the stored user information. After the wireless device ID is associated with the user's information, the user may access their information from the wireless device 500 having this wireless device ID in step 780.

In step 790, the wireless device 500 accesses the central server 200 and unlocks the stored information responsive to receipt of a "key" from the wireless device 500. The server 200 may send the information stored on the databases 400 to the wireless device 500 or a terminal in step 795. The server 200 may return a WML page containing the information using a URL. The returned URL may contain all of a user's information encoded within it, which may be Personal, medical history, and/or insurance information. Because some wireless devices limit the length of a URL to a specific number of characters, compression or lookups may be used in a URL containing a user's information, such as for example D=diabetes. Lookups allow for encoding maximum user information.

In one embodiment, the username, password, and wireless device ID are collectively used as a "key" which may be necessary for any subsequent access to user's information. In a separate embodiment, the wireless device ID may be the only "key" required to access the user's information.

An exemplary URL is: http://www.gomed.com/senddate.wml?f=joan?q=simple?l=doe?a=4510.bay.road?tet=1195?d=a.

The above URL is a basic example of the format the URL may take when storing user information, the information may also employ lookup tables and an encryption method to further protect user data in case the user lends the wireless device out and that borrower looks through the user's bookmarks on the device display.

Alternatively, the server 200 may ask the user for destination information. The user may enter destination information to send the medical/insurance information to a terminal, such as but not limited to, a computer in a doctor's office or hospital, or a wireless device in an ambulance or carried by a paramedic. The central server 200 may be adapted to format the information and transmit it to the remote terminal 800 (FIG. 7) via e-mail, fax, or any other appropriate means of communication.

Figure 10:
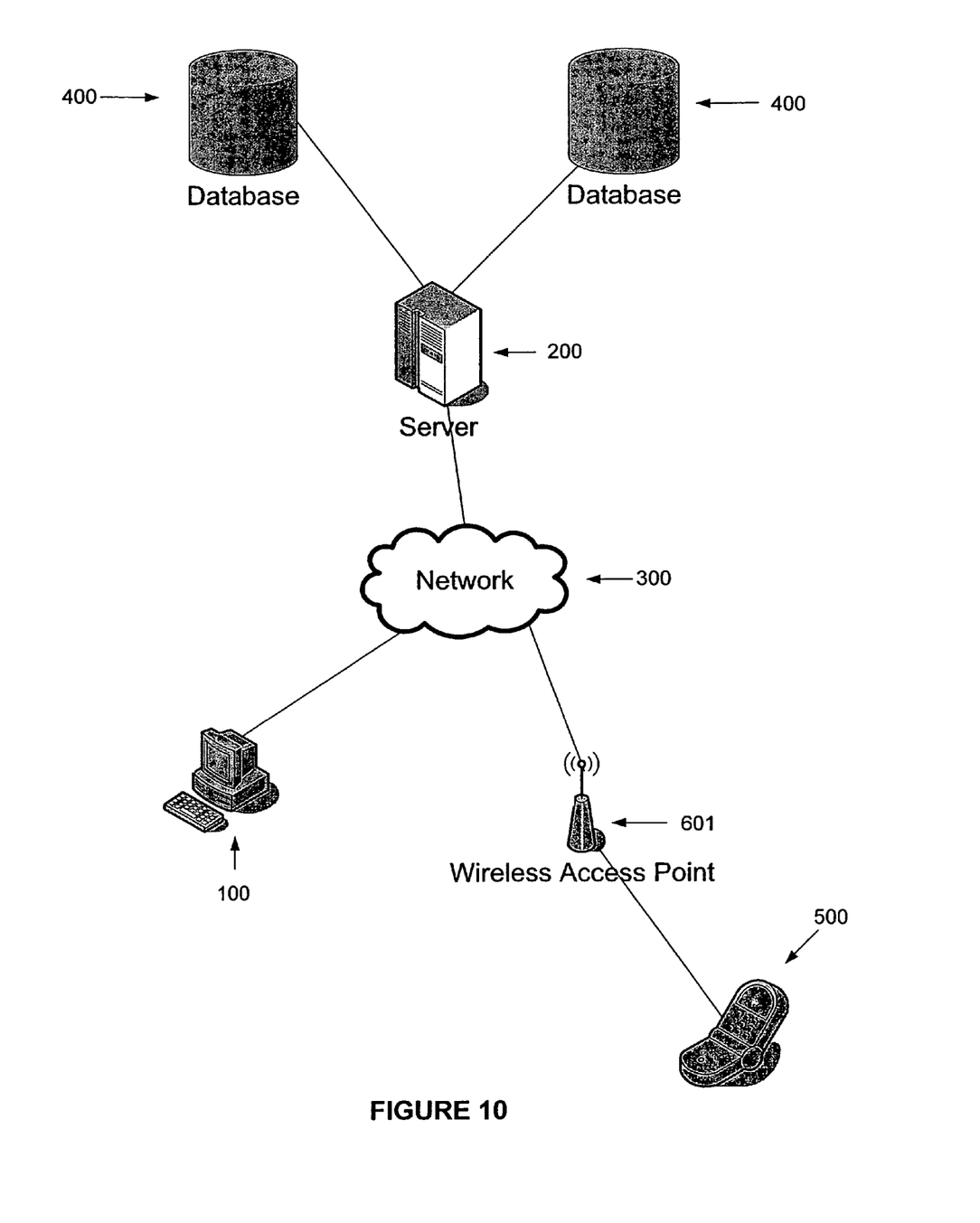
FIG. 10 is schematic diagram illustrating a system for storing information on a wireless device according to an alternative embodiment of the present invention.

FIG. 10 illustrates an alternative embodiment of the present invention in which wireless device 500 accesses the central server 200 by means of a non-cell-based channel, such as an IP-based access point 601.

It will be apparent to those skilled in the art that variations and modifications of the present invention can be made without departing from the scope or spirit of the invention. For example, the present invention could be adapted to store and transmit any type of information on wireless devices, such as car insurance information or business resumes. Thus, it is intended that the present invention cover all such modifications and variations of the invention, provided they come within the scope of the appended claims and their equivalents.

What is claimed is:

1. A method for storing and retrieving information using a wireless telephone having an Internet browser, comprising the steps of:
   accessing a central server, said central server having at least one database associated therewith;
   storing personal, medical or insurance information relating to a person on the central server database;
   storing a password or PIN on the central server database and associating the password or PIN with the stored personal, medical or insurance information;
   accessing the central server with the wireless telephone;
   associating the stored personal, medical or insurance information with a wireless device ID received from the wireless telephone;
   accessing the central server database a second time with the wireless telephone using the wireless telephone Internet browser;
   transmitting a key comprising the wireless device ID and one of the password or PIN from the wireless telephone to the central server; and
   transferring at least a portion of the stored personal, medical or insurance information from the central server to a remote terminal responsive to the receipt at the central server of the key from the wireless telephone.

2. The method of claim 1, wherein the central server is accessed for the storage of the personal, medical or insurance information by a computer terminal using an Internet connection.

3. The method of claim 1, wherein the central server is accessed for the storage of the personal, medical or insurance information by a computer terminal located locally with the central server.

4. The method of claim 1, wherein the wireless device ID comprises a unique hardware ID stored in the wireless telephone.

5. The method of claim 1, wherein the remote terminal is a telefax machine.

6. The method of claim 1, wherein the remote terminal is adapted to receive electronic communication.

7. The method of claim 1 wherein the step of transferring at least a portion of the information from the central server database comprises the step of transferring the information as a URL.

8. The method of claim 1 wherein the step of storing the information in the central server database comprises the step of storing the information in a memory allocated to the storage of personal, medical, or insurance information.

9. The method according to claim 1 further comprising the steps of:
   storing medication reminder information on the central server database; and
   indicating a medication reminder with the wireless telephone in response to the storage of medication reminder information on the central server database.

10. A method for storing information to be retrieved in response to the receipt of a key from a wireless device, comprising the steps of:
   accessing a central server with a remote input device, said central server having a database associated therewith;
   storing information relating to a person in the central server database;
   storing in the database a password or PIN associated with the information;
   accessing the central server with a wireless device and associating a unique hardware ID for the wireless device, the password or PIN, and the stored information at the central server;
   transmitting the unique hardware ID and one of the password or PIN from the wireless device to the central server;
   transmitting at least a portion of the information stored in the database to the wireless device responsive to the receipt of the unique hardware ID and one of the password or PIN by the central server from the wireless device; and
   displaying at least a portion of the information on the wireless device.

11. The method according to claim 10, wherein the information comprises personal, medical, or insurance information.

12. The method according to claim 10, further comprising the step of transmitting at least a portion of the information displayed on the wireless device to a remote terminal.

13. The method according to claim 12, wherein the remote terminal is a telefax machine.

14. The method according to claim 12, wherein the remote terminal is a computer adapted to receive electronic communications.

15. The method according to claim 10 further comprising the step of storing in the wireless device at least a portion of the information displayed thereon.

16. The method according to claim 15 further comprising the step of entering the password or PIN into the wireless device prior to display of at least a portion of the information stored on the wireless device.

17. A method for storing and retrieving information using a wireless telephone having an Internet browser, comprising the steps of:
   accessing a central server, said central server having at least one database associated therewith;
   storing personal, medical or insurance information relating to a person on the central server database;
   storing a password or PIN on the central server database and associating the password or PIN with the stored personal, medical or insurance information;
   accessing the central server with the wireless telephone;
   associating the stored personal, medical or insurance information with a wireless device ID received from the wireless telephone;
   accessing the central server database a second time with the wireless telephone using the wireless telephone Internet browser;
   transmitting a key comprising the wireless device ID and one of the password or PIN from the wireless telephone to the central server; and
   transferring at least a portion of the stored personal, medical or insurance information from the central server to the wireless telephone responsive to the receipt at the central server of the key from the wireless telephone.

18. The method according to claim 17 further comprising the step of indicating a medication reminder with the wireless telephone in response to the transmission of the key from the wireless telephone to the central server.

* * * * *